US00PP33481P2

(12) United States Plant Patent
Farrow

(10) Patent No.: US PP33,481 P2
(45) Date of Patent: Sep. 14, 2021

(54) ***LAGERSTROEMIA* PLANT NAMED 'FAIRFARLAG'**

(50) Latin Name: *Lagerstroemia indica*
Varietal Denomination: Fairfarlag

(71) Applicant: THE CONARD PYLE COMPANY, West Grove, PA (US)

(72) Inventor: Michael W. Farrow, Warwick, MD (US)

(73) Assignee: THE CONARD PYLE COMPANY, West Grove, PA (US)

( * ) Notice: Subject to any disclaimer, the term of this patent is extended or adjusted under 35 U.S.C. 154(b) by 0 days.

(21) Appl. No.: 17/137,486

(22) Filed: Dec. 30, 2020

(51) Int. Cl.
*A01H 5/00* (2018.01)

(52) U.S. Cl.
USPC ..... Plt./252

(58) Field of Classification Search
USPC ..... Plt./252
See application file for complete search history.

(56) References Cited

PUBLICATIONS

"Shrubs Vines Trees Evergreens Edibles" 2021 Star® Roses and Plants Catalog, published on Feb. 23, 2020, pp. 11,64, and 88.

*Primary Examiner* — Annette H Para
(74) *Attorney, Agent, or Firm* — Panitch Schwarze Belisario & Nadel LLP; Stephany G. Small; Travis W. Bliss

(57) ABSTRACT

A new and distinct variety of *Lagerstroemia* plant, referred to by its cultivar name, 'Fairfarlag', is disclosed. The new variety forms attractive deep pink colored flowers. Attractive, dark green colored foliage is formed. The growth habit is dense and mounded. The new variety is well suited for providing attractive ornamentation in the landscape.

2 Drawing Sheets

Figure 1:
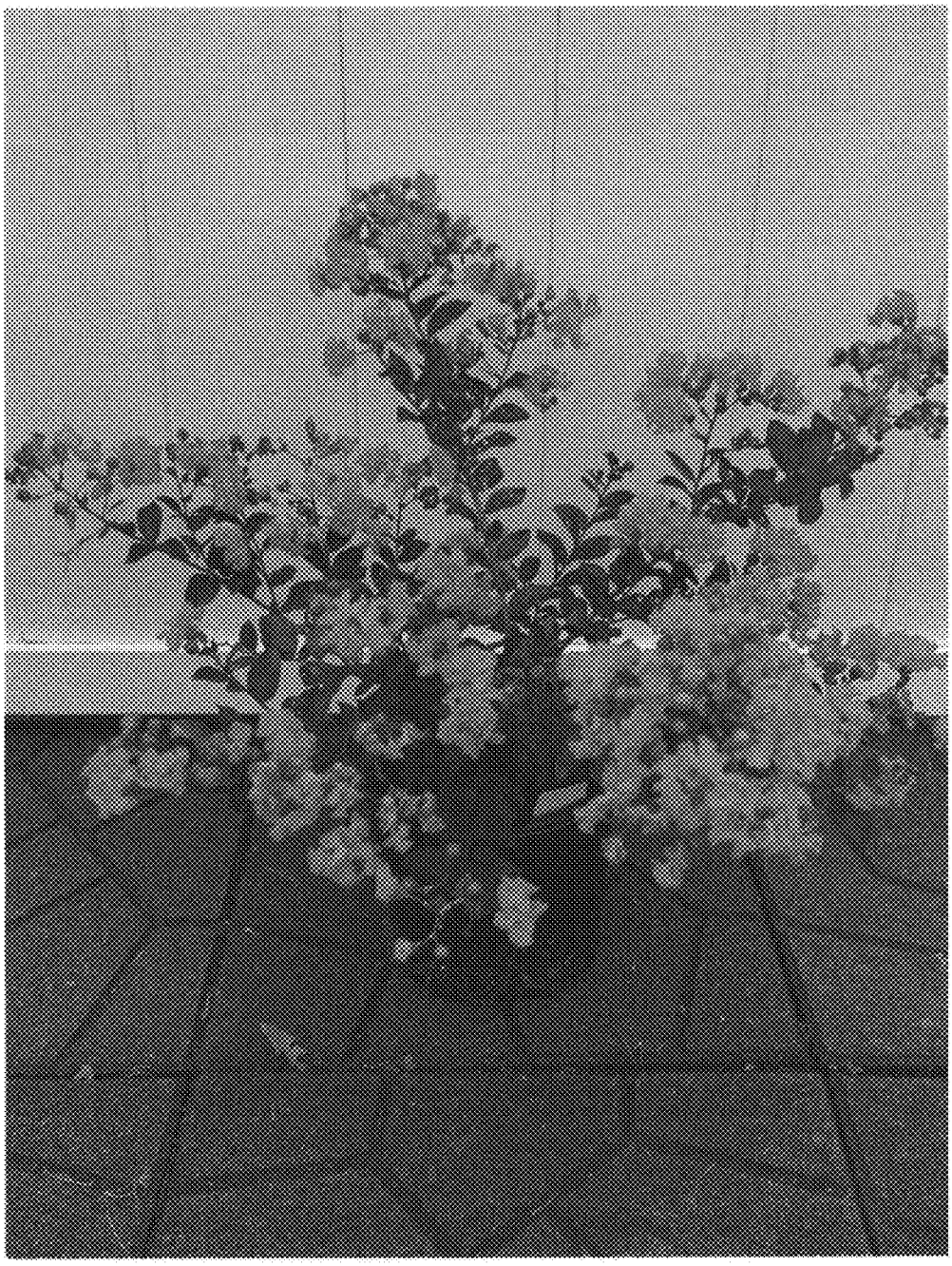

Botanical/commercial classification:
Latin name: *Lagerstroemia indica.*
Varietal denomination: 'Fairfarlag'.

SUMMARY OF THE INVENTION

The new variety of *Lagerstroemia indica* plant originated in a controlled breeding program in Earleville, Md. during 2015. The objective of the breeding program was the development of a series of *Lagerstroemia* cultivars having abundant inflorescences with attractive flower coloration and compact growth habit. The new cultivar was created by open pollination. The female parent (Le., the seed parent) was the 'Twilight' variety (non-patented). The male parent (i.e, the pollen parent) was unknown.

The parentage of the new variety can be summarized as follows:

'Twilight' x unknown variety

The new cultivar was discovered and selected as a single flowering plant from the progeny resulting from the above open pollination during August 2016 in a controlled environment in Earleville, Md. Selective study resulted in the identification of a single plant of the new variety.

It was found that the new variety of *Lagerstroemia* plant of the present invention:

(a) forms deep pink colored flowers,
(b) displays dark green colored foliage, and
(c) exhibits a vigorous, dense and mounded growth habit.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'Twilight' variety (i.e., the seed parent) displays purple colored flowers and an upright growth habit, whereas the new variety provides light pink colored flowers and a dense and mounded growth habit. Moreover, the new variety can also be distinguished from other similar varieties that are commercially available. For instance, the new variety of the present invention can readily be distinguished from the 'Pocomoke' variety (non-patented), as the new cultivar displays a heavier flower set and a more mounding growth habit compared to the 'Pocomoke' variety.

The new variety has been found to undergo asexual propagation by terminal stem cuttings. Asexual propagation by terminal stem cuttings in Cochranville, Pa. since August 2016 has shown that the characteristics of the new variety are stable and are strictly transmissible by such asexual propagation from one generation to another. Accordingly, the new variety undergoes asexual propagation in a true-to-type manner.

The new variety has been named 'Fairfarlag'.

The new variety was first offered for sale in the "SHRUBS VINES TREES EVERGREENS EDIBLES" 2021 *Star® Roses and Plants Catalog*, which was published on Feb. 23, 2020 by the inventor or by another who obtained the new variety directly or indirectly from the inventor.

BRIEF DESCRIPTION OF THE PHOTOGRAPHS

The accompanying photographs show as nearly true as it is reasonably possible to make the same, in a color illustration of this character, typical specimens of the plant and plant parts of the new variety. Colors in the photographs may differ slightly from the color values cited in the detailed description, which accurately describes the colors of the 'Fairfarlag' variety. The plants were approximately 18 weeks old from transplant and were grown in one-gallon containers for four and a half months outside at Cochranville, Pa.

FIG. 1—illustrates a specimen of the plant displaying the overall growth and flowering habit—side view.

Figure 2:
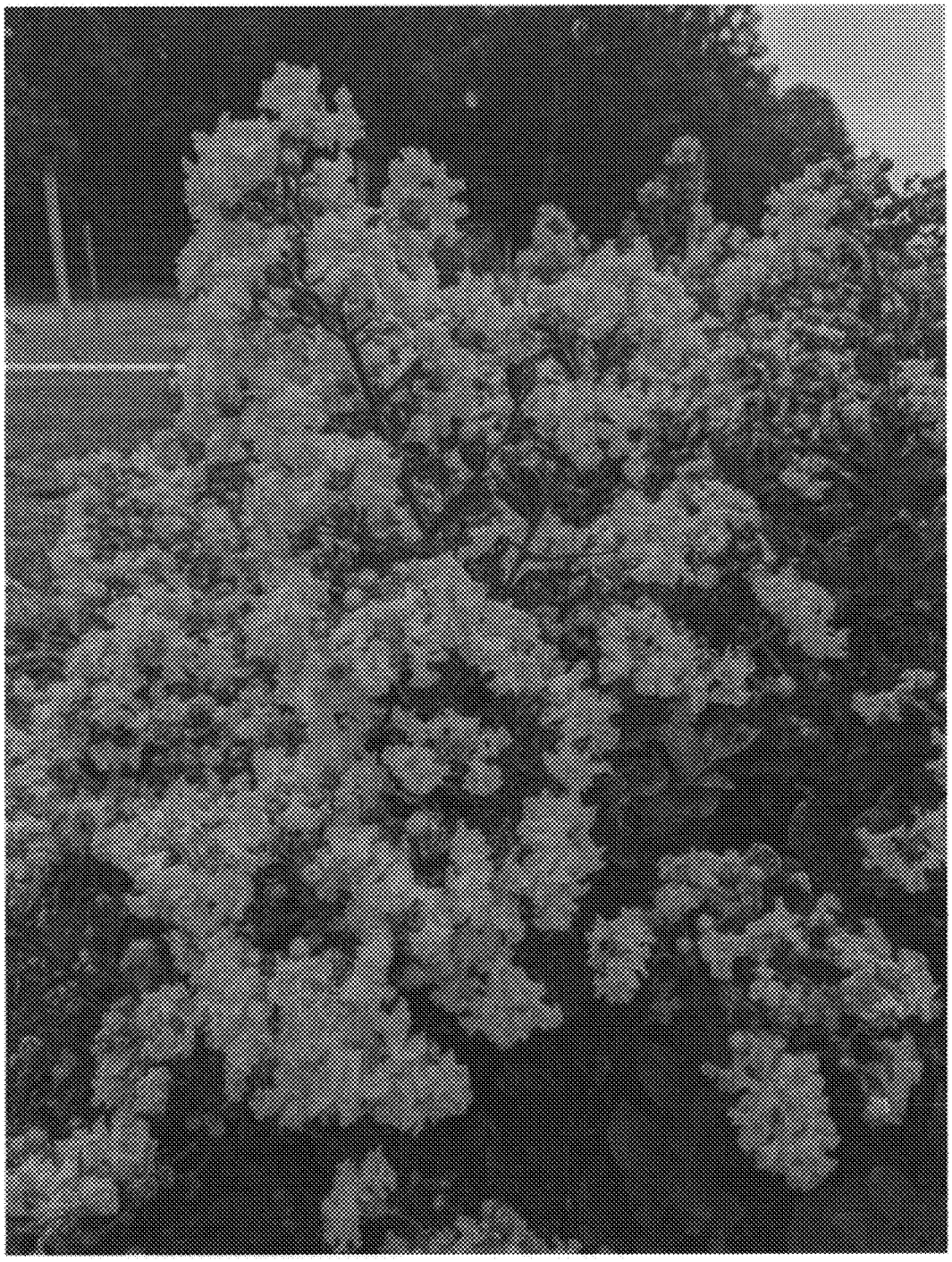

FIG. 2—illustrates specimen of inflorescences.

DETAILED BOTANICAL DESCRIPTION

The chart used in the identification of the colors is that of The Royal Horticultural Society (R.H.S. Color Chart), 2015 edition, London, England. The terminology which precedes reference to the chart has been added to indicate the corresponding color in more common terms. The color values were determined in August 2020 under natural light conditions in Cochranville, Pa. The description is based on the observation of plants which were 18 weeks old from transplant plants produced from stock plants and grown outside in one-gallon containers for four and a half months under conditions comparable to those used in commercial nursery practice in Cochranville, Pa.

Parentage:

*Female parent*.—'Twilight' (non-patented).

*Male parent*.—Unknown.

Propagation:

*Type cutting*.—Terminal cuttings.

*Time to initiate roots*.—Approximately 16 days on average.

*Time to produce a rooted cutting*.—Approximately 39 days on average.

*Root description*.—Fibrous and fine; white to brown in color.

*Rooting habit*.—Freely branching; dense.

Plant:

*Habit*.—Multistemmed deciduous shrub, vigorous and dense mounding growth habit.

*Commercial crop time*.—Approximately 18 weeks from a rooted cutting to finish in a one-gallon container on average.

*Size*.—Approximately 40.0 cm in height from soil level to top of plant plane on average; and approximately 50.0 cm in width on average.

Branches:

*Branching habit*.—Freely branching, pinching enhances branching.

*Quantity*.—Approximately 3 main stems per plant with approximately 3 lateral branches per stem.

*Shape*.—Quadrangulate with rounded wings.

*Strength*.—Strong.

*Arrangement*.—Subopposite to alternate.

*Aspect*.—Erect to 45° angle from main stem.

*Size*.—Length to base of inflorescence: typically 17.0 cm to 22.0 cm on average. — diameter of main stem: approximately 7.0 mm on average. — diameter of secondary stem: approximately 4.0 mm on average. — length of central internode: approximately 1.5 cm on average.

*Texture*.—Young stem is glabrous; mature stem is woody, rough.

Foliage:

*Fragrance*.—None detected.

*Form*.—Simple.

*Arrangement*.—Subopposite to alternate.

Leaves:

*Shape*.—General: ovate to elliptic. — margin: entire. — apex: acute. — base: attenuate.

*Venation*.—Pattern: pinnate.

*Size*.—Length of mature leaf: approximately 4.0 cm on average. — width of mature leaf: approximately 2.5 cm on average.

*Texture*.—Upper and lower surfaces: glabrous.

*Color*.—Upper surface of mature foliage: commonly near Green Group NN137A, with indistinguishable venation. — lower surface of mature foliage: commonly near Green Group NN137C, with venation commonly near Green Group 139D.

*Petiole*.—Length: approximately 1.0 mm on average. — width: approximately 1.5 mm on average. — texture: glabrous. — color: commonly near Yellow-Green Group 152B.

Inflorescence:

*Quantity*.—Approximately 18 inflorescence per plant; variable from 6 to 12 open blooms at a time per inflorescence.

*Type*.—Panicle, flowers self-cleaning.

*Fragrance*.—Faint sweet.

*Aspect*.—Upward to outward.

*Depth or height*.—Approximately 10.0 cm on average.

*Width*.—Approximately 11.0 cm on average. — shape: rounded. — strength: strong. — aspect: erect to about 45° from branch axis.

Flower:

*Bud just before opening*.—Shape: globose. — length: approximately 7.0 mm on average. — diameter: approximately 8.0 mm on average. — color of petals: commonly near Greyed-Red Group 181A.

*Corolla*.—Shape: rotate. — depth: approximately 1.5 cm on average. — diameter: approximately 4.0 cm on average.

*Petals*.—Shape: ovate. margin: crisped, undulating. apex: rounded. base: truncate. — length: approximately 1.5 cm on average. — width: approximately 1.5 cm on average. — texture of upper and lower surfaces: glabrous. — color of upper and lower surfaces: commonly near Red Group 51A.

*Calyx*.—Shape: round. — depth: approximately 1.0 cm on average. — diameter: approximately 1.2 cm on average.

*Sepals*.—Length: approximately 5.0 mm on average. — width: approximately 4.0 mm on average. — shape: triangular. — apex: acute. — base: truncate. — margin: smooth, entire. — upper surface: texture: glabrous. color: commonly near Greyed-Green Group 193C toward the base and transitioning to near Red Group 51D toward the apex. — lower surface: texture: glabrous. color: commonly near Greyed-Red Group 181B.

*Pedicels*.—Strength: strong. — length: approximately 1.2 cm on average. — diameter: approximately 2.0 mm on average. — aspect: erect, to about 45° from peduncle. — texture: glabrous. — color: commonly near Greyed-Red Group 181A.

*Reproductive organs*.—Androecium: Stamen: approximately 35 per flower, length is approximately 1.2 cm on average. filament: color is commonly near Red Group 39B. anther: shape is narrow oblong, dorsifixed, length is approximately 1.5 mm on average, and color is commonly near Yellow-Orange Group 22A. pollen: amount is abundant and coloration is commonly near Yellow-Orange Group 15B. — gynoecium: pistil: commonly 1 per flower, length is approximately 2.0 cm on average. stigma: shape is rounded, color is commonly near Green Group 133A. style: length is approximately 1.7 cm on average and coloration is commonly near Red Group 47B. ovary: length is approximately 2.0 mm on average and coloration is commonly near Yellow Group 3C. — seed and fruit: none have been observed to date.

Development:

*Flowering season*.—Flowers in mid-summer through early fall.

*Lastingness of individual inflorescence on the plant*.—Approximately 1 to 2 weeks on average.

*Tolerance to disease and pest*.—Good resistance to powdery mildew (*Erysiphe lagerstroemia*).

*Hardiness zone*.—USDA Zone 6b (−5° F.).

The new 'Fairfarlag' variety has not been observed under all possible environmental conditions to date. Accordingly, it is possible that the phenotypic expression may vary somewhat with changes in light intensity and duration, cultural practices, and other environmental conditions.

I claim:

1. A new and distinct cultivar of *Lagerstroemia* plant characterized by the following combination of characteristics:

(a) forms deep pink colored flowers, (b) displays dark green colored foliage, and (c) exhibits a vigorous, dense and mounded growth habit; substantially as herein shown and described.

* * * * *